United States Patent
Evans

(10) Patent No.: US 10,018,569 B2
(45) Date of Patent: Jul. 10, 2018

(54) OPTICAL FIBER COMMUNICATIONS WITH COMPOSITE STRUCTURAL MONITORING FOR DETERMINING DAMAGED STRUCTURE BASED ON THE ANALYSIS OF OPTICAL SIGNAL

(71) Applicant: NORTHROP GRUMMAN SYSTEMS CORPORATION, Falls Church, VA (US)

(72) Inventor: David W. Evans, Signal Hill, CA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 324 days.

(21) Appl. No.: 15/153,565

(22) Filed: May 12, 2016

(65) Prior Publication Data
US 2017/0328840 A1 Nov. 16, 2017

(51) Int. Cl.
*G01N 21/88* (2006.01)
*G01N 21/27* (2006.01)
(Continued)

(52) U.S. Cl.
CPC ......... *G01N 21/8806* (2013.01); *B64D 45/00* (2013.01); *G01N 21/27* (2013.01);
(Continued)

(58) Field of Classification Search
CPC ........... B64D 45/00; G01N 2021/8472; G01N 21/8806; H04B 10/07953; H04B 10/25
(Continued)

(56) References Cited

U.S. PATENT DOCUMENTS 5,015,842 A  5/1991 Fradenburgh et al.
5,299,271 A  3/1994 Hildebrand
(Continued)

FOREIGN PATENT DOCUMENTS

CN  101561400 A  10/2009
WO  2011/104319 A1  9/2011

OTHER PUBLICATIONS

McAdam, G. et al., "Fiber Optic Sensors for Detection of Corrosion within Aircraft" Structural Health Monitoring, 2005, vol. 4.1, pp. 47-56.
(Continued)

*Primary Examiner* — Que T Le
(74) *Attorney, Agent, or Firm* — John A. Miller; Shumaker, Loop & Kendrick, LLP

(57) ABSTRACT

A method for detecting defects in a composite structure, such as in an aircraft structure, that includes sending an optical signal down an optical fiber embedded in the composite structure and analyzing the optical signal at a detector. If it is determined that the optical signal is turning on and off or an increase in the bit error rate is occurring at the detector, the composite structure may be delaminating or the composite structure may be somehow damaged. If it is determined that the composite structure is damaged, the optical signal can be sent down a different optical fiber that may not be at a location where the composite structure is damaged, and a continuous beam of light can be sent down the optical fiber that is at the damaged part of the composite structure to determine whether the damage is increasing.

20 Claims, 1 Drawing Sheet

(51) Int. Cl.
*B64D 45/00* (2006.01)
*H04B 10/079* (2013.01)
*H04B 10/25* (2013.01)
*G01M 17/007* (2006.01)
*G01N 21/84* (2006.01)

(52) U.S. Cl.
CPC ....... *H04B 10/07953* (2013.01); *H04B 10/25* (2013.01); *B64D 2045/0085* (2013.01); *G01M 17/007* (2013.01); *G01N 2021/8472* (2013.01); *G01N 2201/088* (2013.01)

(58) Field of Classification Search
USPC ........................................ 250/227.14, 227.18
See application file for complete search history.

(56) References Cited

U.S. PATENT DOCUMENTS

| | | | |
|---|---|---|---|
| 5,299,273 | A | 3/1994 | Evans |
| 6,587,621 | B2 | 7/2003 | Weaver |
| 7,888,813 | B2 | 2/2011 | Stoner |
| 9,088,149 | B2 | 7/2015 | Carroll |
| 9,170,172 | B2 * | 10/2015 | Hunt .................... G01M 11/086 |
| 9,193,313 | B2 | 11/2015 | Erb |
| 9,274,025 | B2 | 3/2016 | Okoli et al. |
| 2010/0332161 | A1 | 12/2010 | Bulumulla |
| 2016/0116366 | A1 | 4/2016 | Da Silva et al. |

OTHER PUBLICATIONS

Betz, Daniel et al., "Test of a Fiber Bragg Grating Sensor Network for Commercial Aircraft Structures" Optical Fiber Sensors Conference Technical Digest, 2002, IEEE, pp. 55-58.

LeBlanc, M. et al. "Development of a Fibre Optic Damage Detection System for an Aircraft Leading Edge" Fiber Optic Smart Structures and Skins II, 1989, SPIE vol. 1170, pp. 196-204.

Measures, R. M. et al., "Structurally Integrated Fiber Optic Damage Assessment System for Composite Materials" Fiber Optic Smart Structures and Skins, 1988, SPIE vol. 986, pp. 120-129.

DiSante, Raffaella, "Fibre Optic Sensors for Structural Health Monitoring of Aircraft Composite Structures: Recent Advances and Applications" Sensors, ISSN 1424-8220, 2015, pp. 18666-18713.

Lam, Pau-Man, et al. "Acousto-Ultrasonic Sensing for Delaminated GFRP Composites Using an Embedded FBG Sensor" Optics and Lasers in Engineering 47, 2009, pp. 1049-1055.

Zhou, G. et al. "Damage Detection and Assessment in Fibre-Reinforced Composite Structures with Embedded Fibre Optic Sensors—review" Smart Materials and Structures, 11, 2002, pp. 929-939.

Liu, Kexing et al. "Acoustic Emission Detection for Composite Damage Assessment using Embedded Ordinary Single-Mode Fiber-Optic Interferometric Sensors", 1990.

* cited by examiner

OPTICAL FIBER COMMUNICATIONS WITH COMPOSITE STRUCTURAL MONITORING FOR DETERMINING DAMAGED STRUCTURE BASED ON THE ANALYSIS OF OPTICAL SIGNAL

BACKGROUND

Field

This invention relates generally to a system and method for detecting defects in a composite structure using optical fibers embedded in the structure and, more particularly, to a system and method for detecting defects in a composite aircraft structure using optical fibers embedded in the structure without the burden of constantly checking for damage.

Discussion

It is necessary that most aircraft structures be very strong, lightweight and corrosion resistant. To this end, advances in materials have led to many aircraft structures being made of composite materials, such as carbon fiber resin composites, fiberglass composites, etc. A typical carbon fiber composite may include two opposing face sheets, where each face sheet is formed by a number of carbon fiber ply layers bonded together with a resin, and where a honeycomb structure also formed of the carbon fiber ply layers is provided between the face sheets so that the primary structural integrity of the structure is at its outer edges and the honeycomb structure provides the desired stiffness and lightweight properties.

Often times when a composite structure is damaged or becomes defective in some way, it delaminates where layers in the composite structure separate, thus reducing the integrity of the structure. This type of delamination damage to a composite structure can be invisible during inspection of the structure because composites tend to return to their original shape when stress on the structure is removed, which makes the damage difficult to identify. In other words, for this type of defect on a composite aircraft structure, the specific component may be appear visually proper when the aircraft is on the ground and not moving, but under stress and vibration, the delamination will vibrate and could continue to grow without being detected. This characteristic has caused a substantial delay in the use of composites on aircraft.

A typical aircraft will also include many wires and cables that electrically couple various devices, such as avionics devices, control devices, communications devices, etc. The amount of electrical wire that is required will add significant weight to the aircraft and as such, certain types of aircraft have been developed that include optical fibers for carrying data and other messages. Optical fibers are very light and delicate requiring some form of conduit to protect them from being damaged. Fibers embedded in a structure obtain their protection from the structure itself such that providing fibers in a composite is nearly free of added weight. If an optical fiber is traveling through a part of a composite structure that is delaminating, the fiber could crack and separate causing light passing through the fiber to be modulated by the damaged area separating and recovering. It has been observed that a crack or other damage to a fiber may still allow light to pass through the fiber when the structure is not under stress.

DETAILED DESCRIPTION OF THE EMBODIMENTS

The following discussion of the embodiments of the invention directed to a system and method for detecting defects in a composite structure using optical fibers embedded in the structure is merely exemplary in nature, and is in no way intended to limit the invention or its applications or uses. For example, the discussion herein specifically talks about the composite structure being an aircraft structure. However, as will be appreciated by those skilled in the art, the composite structure may be employed for other applications.

As will be discussed in detail below, the present invention proposes using optical fibers configured in a composite structure to detect whether the composite structure has been damaged, whether that damage is increasing and when the structure may fail. For example, if the structure is delaminating where sometimes a light beam propagating down the optical fiber is present at the detector when the structure is not under stress and sometimes it is not present at the detector when the structure is under stress, the loss of light can be an indication that delamination is occurring and the frequency of when the light beam is being received and not being received at the detector can be analyzed through spectral analysis or otherwise to determine whether the rate at which the delamination is occurring is increasing.

The optical fiber can be used to transmit data messages from one location in the aircraft to another, where the bit error rate (BER) of those data messages can be monitored such that if the BER of the beam is significantly increasing at any point of time, it can be assumed that there is damage, such as delamination, to the structure at least in the area where the optical fiber is provided. If the BER indicates that there is damage to the composite structure, the transfer of data can be switched to another undamaged optical fiber. The transmitting source of the beam connected to the damaged fiber can be configured to then produce steady unmodulated light. The detector connected to the damaged fiber will still see modulated light, which is now modulated by the damage to the fiber and can be monitored and characterized. Changes in the characteristics of modulation coming from the damage could indicate that the damage is growing, where the rate of change of the modulation reflects the rate the damage is propagating through the structure. Through experimentation, the changes in modulation can be used to estimate the time remaining until the damaged structure fails.

Figure 1:
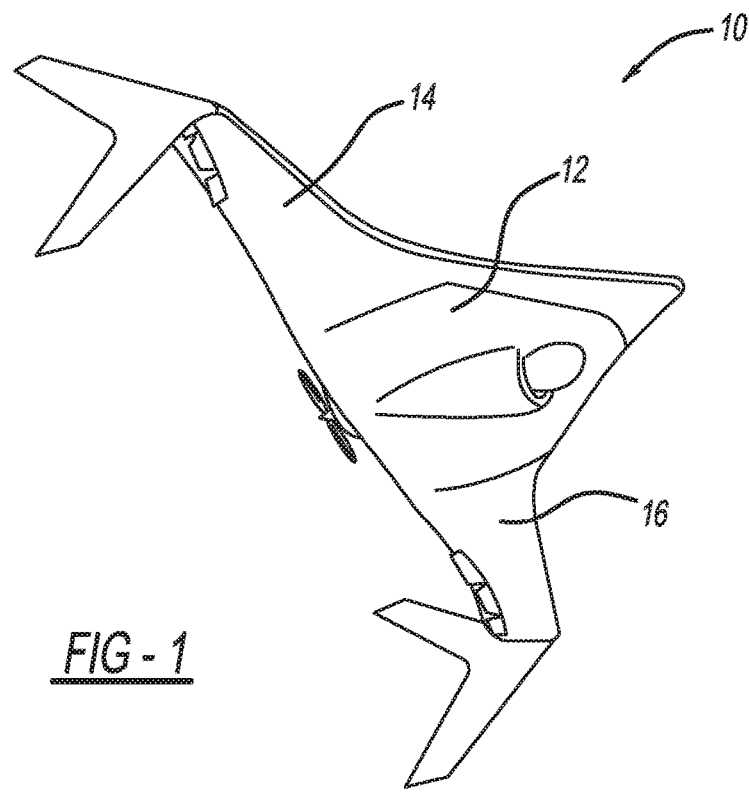
FIG. 1 is an isometric view of an aircraft including composite structures.

FIG. 1 is an isometric view of an aircraft 10 including an aircraft body 12, aircraft wings 14 and 16, and other aircraft structural components. The aircraft 10 is intended to represent any modern military or commercial aircraft that includes one or more composite structures, such as carbon fiber structures, that provide high strength, corrosion resistance and low weight. The aircraft 10 is also intended to represent an aircraft that may employ optical fibers for carrying data, communications signals, etc.

Figure 2:
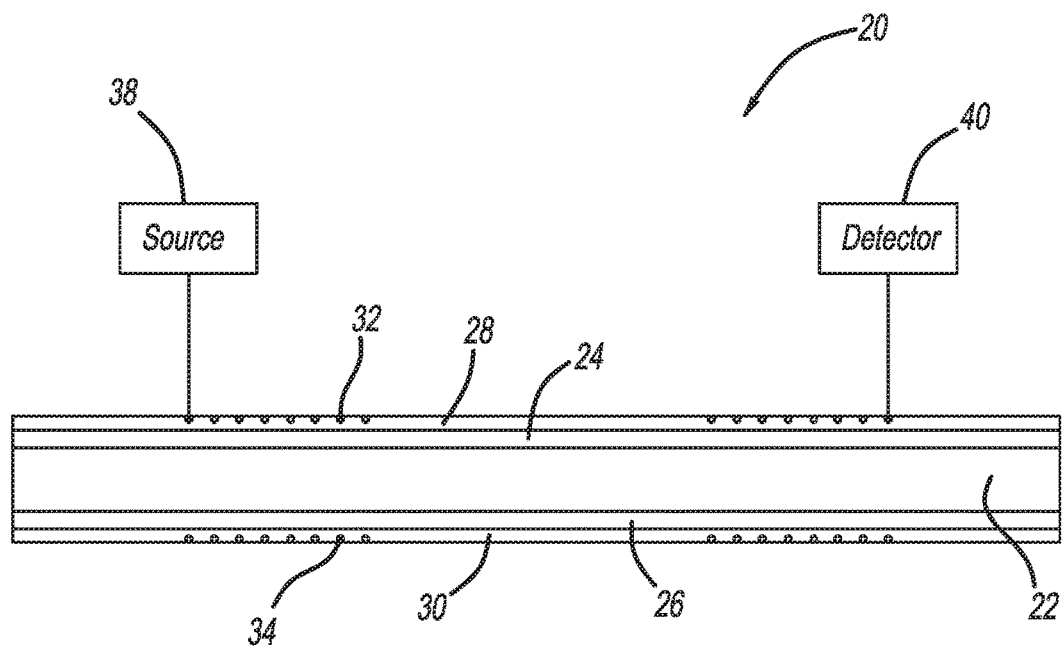
FIG. 2 is a profile view of a composite structure that could be on the aircraft shown in FIG. 1, and that includes optical fibers that are operable to detect defects in the structure.

FIG. 2 is a profile view of a composite structure 20 that is intended to represent a portion of any composite structure on the aircraft 10 or otherwise, and is intended to be a general representation of many different types of composite structures that could be provided in art. In this design, the composite structure 20 includes a center core 22 that could be, for example, a carbon fiber honeycomb structure, structural foam, etc. The center core 22 is sandwiched between opposing conductive layers 24 and 26, such as aluminum layers, that could operate to transfer power and ground signals to various devices, avionic bays, communications systems, etc. on the aircraft 10. For example, the conductive layers 24 and 26 could be used to distribute three-phase AC power, which could be rectified at each device, or DC power could be routed to each device as the simplest distribution case. Other combinations of power can be distributed with increasing complexity in a vehicle structure.

An insulating composite network layer 28 is formed to the conductive layer 24 opposite to the core 22, and an insulating composite network layer 30 is formed to the conductive layer 26 opposite to the core 22. Optical network communications technologies could be embedded into the composite network layers 28 and 30, which are generally represented here as embedded optical fiber 32 in the layer 28 and embedded optical fiber 34 in the layer 30. The optical fibers 32 and 34 could provide point-to-point communications between various devices. In one embodiment, bare fiber is provided inside the composite layers 28 and 30 and connectors (not shown) are bonded to the composite material post material cure. The optical fibers 32 and 34 are positioned so as to provide data communications between various devices and be provided in the layers 28 and 30 at locations where delamination and other defects or damage may be more probable. In other words, the fibers 32 and 34 can be strategically located in the layers 28 and 30 such as, for example, be configured in a serpentine manner across areas of the structure 20 that may be subject to damage. The optical fibers 32 and 34 are intended to represent single fibers, multiple fibers, parallel fibers, redundant fibers, serpentine fibers, etc. strategically located within the network layers 28 and 30 consistent with the discussion herein.

In this non-limiting embodiment, an optical source 38 provides an optical signal on the fiber 32 that is received by an optical detector 40 at an opposite end of the fiber 32. The optical source 38 is intended to represent any type of signal generating apparatus or device that sends optical signals down the fiber 32 for transfer of data or otherwise, and the detector 40 is intended to represent any receiving device, such as in an avionics bay on the aircraft 10, that is intended to receive the messages or data.

If there is a structural defect in the composite layer 28 or 30, where layers inside the composite layer 28 or 30 may be separating and delaminating, those delaminations may affect the signal propagation in the fibers 32 and 34. As discussed above, stress on the structure 20, such as from vibrations of the aircraft 10, may cause the delaminating layers to prevent light from propagate down the fiber 32 or 34, and when that stress is removed, light may again propagate down the fiber 32 or 34. Particularly, if a structural defect, such as periodic delaminations, occurs in the layer 28 that causes damage to the fiber 32, the optical signal propagating along the fiber 32 may fail to be transmitted at different points in time depending on the type of damage, the degree of the damage, the stresses on the structure 20, etc. The optical signal may return as stresses on the structure 20 come and go. This on/off switching of the optical signal propagating on the fiber 32 has a frequency spectrum depending on how fast the on/off switching is occurring, and that frequency spectrum can be analyzed in the detector 40 to determine whether the defect is severe and whether it is increasing. For example, a Fourier transform or other spectrum analysis can be employed to convert the on/off switching of the light beam over time in to the frequency domain, which can then be analyzed to identify whether the damage is increasing. That analysis can also be employed to give an estimate of when the structure 20 may fail.

Additionally or otherwise, a bit error rate (BER) of the optical signal can be monitored in the detector 40, where a high enough BER may be an indication that damage has occurred to the fiber 32 or 34. If a high BER is detected, then the transmission of the data can be sent down another fiber that may not be damaged. The source 38 connected to the damaged fiber can be configured to then produce steady unmodulated light on the damaged fiber 32. The detector 40 will still see light that is now modulated by the damage to the fiber 32, which can be monitored and characterized. Changes in the characteristics of modulation coming from the damage could indicate that the damage is growing, where the rate of change of the modulation reflects the rate the damage is propagating through the structure 20.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for detecting defects in a composite structure, said method comprising:
   providing at least one optical fiber in the composite structure;
   sending an optical signal down the at least one optical fiber;
   detecting the optical signal propagating down the fiber at a detector;
   determining that the optical signal is turning on and off at the detector;
   determining that the composite structure is damaged because of the turning on and off of the signal; and
   determining whether the damage to the composite structure is increasing by analyzing changes in spectral content of how often the detected optical signal turns on and off.

2. The method according to claim 1 further comprising determining that a bit error rate (BER) of the optical signal has significantly increased at the detector, wherein determining that the composite structure is damaged includes determining that the composite structure is damaged if the increased BER is detected.

3. The method according to claim 2 wherein providing at least one optical fiber includes providing a plurality of optical fibers, and wherein if it is determined that the composite structure is damaged, sending the optical signal down an undamaged optical fiber to the detector.

4. The method according to claim 1 further comprising providing a continuous unmodulated light beam on the at least one optical fiber if it is determined that the composite structure is damaged so as to observe the spectral content of the detected optical signal caused by the damage.

5. The method according to claim 1 further comprising predicting when the composite structure will fail based on changes in the spectral content of the detected optical signal.

6. The method according to claim 1 wherein determining that the composite structure is damaged includes determining that the composite structure is delaminating.

7. The method according to claim 1 wherein providing at least one optical fiber includes providing at least one optical fiber configured in a serpentine manner.

8. The method according to claim 1 wherein the composite structure is a carbon fiber composite structure.

9. The method according to claim 1 wherein the composite structure is on an aircraft.

10. A method for detecting defects in a composite structure, said method comprising:
providing at least one optical fiber in the composite structure;
sending an optical signal down the at least one optical fiber;
detecting the optical signal propagating down the fiber at a detector;
identifying a bit error rate (BER) of the optical signal at the detector;
determining whether the BER has significantly increased; and
determining that the composite structure is damaged as a result of the increase in the BER.

11. The method according to claim 10 wherein providing at least one optical fiber includes providing a plurality of optical fibers, and wherein if it is determined that the composite structure is damaged, sending the optical signal down a different optical fiber to the detector.

12. The method according to claim 10 further comprising providing a continuous unmodulated light beam down the at least one optical fiber if it is determined that the composite structure is damaged so as to observe the spectral content of the detected optical signal.

13. The method according to claim 12 further comprising predicting when the composite structure will fail based on changes in the spectral content of the detected optical signal.

14. The method according to claim 10 wherein determining that the composite structure is damaged includes determining that the composite structure is delaminating.

15. The method according to claim 10 wherein providing at least one optical fiber includes providing at least one optical fiber configured in a serpentine manner.

16. The method according to claim 10 wherein the composite structure is a carbon fiber composite structure.

17. The method according to claim 10 wherein the composite structure is on an aircraft.

18. A method for detecting defects in a composite structure, said method comprising:
providing a plurality of optical fibers in the composite structure;
sending an optical signal down one of the optical fibers;
detecting the optical signal propagating down the one optical fiber at a detector;
analyzing the optical signal at the detector;
determining that the composite structure is damaged based on the analysis of the optical signal; and
sending the optical signal down another one of the optical fibers if it is determined that the one optical fiber is damaged.

19. The method according to claim 18 wherein analyzing the optical signal includes determining that the optical signal is turning on and off and determining whether the damage to the composite structure is increasing by analyzing changes in a spectral frequency of how often the detected optical signal turns on and off.

20. The method according to claim 18 wherein analyzing the optical signal includes determining that a bit error rate (BER) of the optical signal has significantly increased.

* * * * *